US006577390B1

(12) United States Patent
Efthimion

(10) Patent No.: US 6,577,390 B1
(45) Date of Patent: Jun. 10, 2003

(54) CONTINUOUS EMISSIONS MONITOR OF MULTIPLE METAL SPECIES IN HARSH ENVIRONMENTS

(75) Inventor: Phillip C. Efthimion, Bedminster, NJ (US)

(73) Assignee: Efthimion Emerging Industries, LLC, Bedminster, NJ (US)

( * ) Notice: Subject to any disclaimer, the term of this patent is extended or adjusted under 35 U.S.C. 154(b) by 0 days.

(21) Appl. No.: 10/031,527
(22) PCT Filed: Jul. 21, 2000
(86) PCT No.: PCT/US00/19930
§ 371 (c)(1),
(2), (4) Date: Jan. 17, 2002
(87) PCT Pub. No.: WO01/07897
PCT Pub. Date: Feb. 1, 2001

Related U.S. Application Data
(60) Provisional application No. 60/145,341, filed on Jul. 23, 1999.

(51) Int. Cl.[7] ............................................. G01N 21/73
(52) U.S. Cl. ...................................................... 356/316
(58) Field of Search .......................................... 356/316

(56) References Cited
U.S. PATENT DOCUMENTS 3,843,257 A    10/1974   Wooten
5,242,143 A     9/1993   Nagashima et al.
5,479,254 A    12/1995   Woskov et al. ............. 356/316
5,596,405 A  *  1/1997   Seltzer et al. ............... 356/316
5,671,045 A     9/1997   Wosakov et al. ........... 356/316
5,825,485 A    10/1998   Cohn et al. .................. 356/316
5,854,431 A    12/1998   Linker et al.
5,909,277 A     6/1999   Woskov et al. ............. 356/316
5,986,757 A  * 11/1999   Seltzer ........................ 356/316

* cited by examiner

Primary Examiner—F. L. Evans
(74) Attorney, Agent, or Firm—Woodbridge & Associates; Stuart H. Nissim

(57) ABSTRACT

A continuous emissions monitor for the measurement of vapor phase and particulate-based metals in gas streams such as those at coal-fired utility plants, incinerators and manufacturing facilities, in which a pulsed plasma source (10), utilizing a resonant reentrant microwave cavity (12) which is powered by a microwave generator (34), operates at sub atmospheric pressures (<50 Torr.) by using a pump (48) in order to eliminate quenching of the light emission processes by other species in the gas stream and reduce the background emission and where the pulsed operation of the source reduces background light emission from oxides of nitrogen produced in plasma sources operating with nitrogen and oxygen gases thus enhancing the contrast and signal-to-background; resulting in the instrument having a minimum detection level of 0.01 micrograms/m−3 for mercury, as well as, other metal elements such as arsenic and selenium, and requiring less than 10 Watts of microwave power.

20 Claims, 9 Drawing Sheets

CONTINUOUS EMISSIONS MONITOR OF MULTIPLE METAL SPECIES IN HARSH ENVIRONMENTS

This application claims the benefit of Provisional application Ser. No. 60/145,341, filed Jul. 23, 1999.

BACKGROUND OF THE INVENTION

This invention relates to a device to measure mercury and other metals in flue gas from municipal waste incinerators, electric power utility plants, and manufacturing plants at concentrations as low as 10 parts per trillion (0.1 micrograms/m$^{-3}$).

DESCRIPTION OF THE RELATED ART

The 1990 Clean Air Act Amendments and other legislation have raised the concerns over low trace concentrations of metals, especially mercury, in flue gas from electrical generation plants, municipal waste incinerators, and heavy industry. Monitoring will be used to determine the extent of the environmental impact and offers the possibility of empirically minimizing it. In particular, mercury has been found in significant quantities in the lakes and streams of the mid-west of the United States. The source of this mercury has been found to be from the air emissions from large stationary combustion systems. Technology to monitor the levels of mercury may be required by regulations and by technology to control emission levels. The mercury levels at incinerators will be in the range of 0.1–10 parts per billion. However, the levels at electric power utility plants are only 0.03–1.0 parts per billion. For an instrument to measure the lower levels of mercury, for example, it must have a minimum sensitivity on the order of 10 parts per trillion. Furthermore, the instrument must make measurements on flue gas that contains many different molecular gas species that can compromise the measurement of the trace metals, especially mercury.

One approach to measuring metals in gas streams uses plasma emission spectroscopy. U.S. Pat. Nos. 5,479,254 and 5,671,045 describe a device using high-powered (300 Watts) and high-pressure microwave plasma emission spectroscopy to measure metals in gas streams. The plasma source is continuous in operation. The device uses a shorted-waveguide as the plasma source and it is inserted in the gas stream. A microwave tuner is used to couple the high-powered microwaves to the shorted-waveguide. A high-resolution spectrometer (0.01 nm) is used to make the measurements. In U.S. Pat. No. 5,671,045 the device is modified for operation in harsh gas and high-temperature environment. There are no provisions for reducing competing emission from flue gas components nor enhancing the metals emission. The high-pressure operation requires the high microwave power to sustain the plasma discharge. There is no disclosure of measuring mercury. There are examples of measuring magnesium, chromium, and iron in a high temperature furnace as well as the laboratory.

U.S. Pat. No. 5,909,277 represents an improvement to the two patents described above (U.S. Pat. Nos. 5,479,254 and 5,671,045). One improvement is to swirl the gas flow for improved plasma confinement. A nebulizer was added to provide a controlled amount of an element to the device for its calibration. There are no teachings or suggestions to reduce competing emission for flue gas components or enhancing the metals emission.

The same approach is employed for a portable field unit for measuring metals in gas streams. U.S. Pat. No. 5,825,485 describes the same device as in U.S. Pat. No. 5,479,254 described above, but uses a pulsed microwave power supply to decrease power consumption so that it can operate off of batteries which can lighten and shrink the size of the instrument to make the device portable. Again, there are no explicit provisions for reducing competing emission from flue gas components nor enhancing the metals emission. There are no examples of measurements or mentioning of detection levels.

U.S. Pat. No. 3,843,257 is one of the first uses of a microwave emission detector to analyze metals and non-metallic compositions. It operated at pressures of 1 Torr and less where there was an increase of sensitivity. The microwave power was applied continuously and there were no other provisions to improve instrument sensitivity or reduce competing background emission. There are no examples of measurements or mention of detection levels.

To help measure particles in a gas stream U.S. Pat. No. 5,854,431 describes a screen to collect particles. After collection the screen is heated to release vapors and particles for analysis in a particle or vapor detector, such as an ion mobility detector. The device is a particle pre-concentrator utilizing a screen.

U.S. Pat. No. 5,242,143 improves the measurement of trace constitutes in gases with a pre-concentration apparatus. The apparatus uses a sorbent where trace gases are sampled at high pressure near atmospheric pressure and desorbs in a carrier gas at low pressure and low flow rates. In this case the relative mass of the trace constitutes in the carrier gas is much greater than in the sample gas, a clear benefit for a mass spectrometer benefit.

The approaches used in the art do not deal with the specific means of reducing interfering emission from flue gas, or means of reducing quenching of metals emissions of interest. These two effects prevent sensitive measurement of metals and specifically mercury at concentrations as low as 10 parts per trillion in flue gas.

SUMMARY OF THE INVENTION

The present invention measures metals in gas streams by employing plasma emission spectroscopy. Plasma emission spectroscopy by itself, however, is insufficient for measuring concentrations as low as 10 parts per trillion in flue gas because of a number of physical issues. Flue gas consists of an ensemble of gases including nitrogen, oxygen, carbon dioxide, sulfur dioxide, nitric oxide, and nitrous oxide. Very high concentrations of water vapor (18%) are also present.

The plasma source is based upon a resonant-high-intensity reentrant microwave cavity (FIGS. 1a and 1b). The reentrant cavity is cylindrical in shape with a coaxial center conductor connected at one end of the cylinder and on the other end is a small gap. The plasma is formed in the small gap area. The height of the cylindrical part is adjusted to match the resonant condition for a pure coaxial cavity. The size of the gap is adjusted to match the resonant condition for the reentrant cavity. There is a small aperture in the cylinder's wall for the microwave power to flow into the cavity from the microwave generator. The microwave power flows through a waveguide that is connected to the microwave cavity. There is a quartz window in the waveguide to provide a vacuum seal and allow the transmission of the microwave power from the generator to the plasma source (FIG. 1b). Alternately, the window can also be placed in the cavity in the form of a circular quartz tube mounted through the center conductor and exhaust hole in the cavity (FIG. 1a). In addition, the waveguide can be simply replaced with a coaxial wire feed from the power source. The plasma source can be designed to operate in the range of about 30–10,000 MHz. Measurements are made by pulling a gas stream into the cavity with use of a pump. The gas enters the cavity through the center conductor through a small hole and flows into the plasma region. The gas then exits the cavity through a small hole on the opposite side wall. The instrument can also be built with cylindrical and other microwave cavities.

A first configuration is shown in FIG. 2. A sampling probe is mounted in a flue duct to sample the gas stream. An optional filter may follow the probe to remove particulate matter from the gas stream. A heated sample line delivers the gas stream to the plasma source. A flow meter or a flow restriction before the plasma source regulates the gas flow. The plasma source is pulsed to enhance the trace metal signal compared to plasma emission background. The ultra-violet light emanating from the plasma is coupled to a spectrometer with either a fiber optic cable or a lens. The spectrometer resolves the light intensity from the trace metal line (for example, the mercury line near 253.65 nm) and the background light intensity near the trace metal line. These two light intensities are measured with detectors on the output of the spectrometer. The two light intensities are integrated over many pulses, for example, by box-car averaging techniques. The trace metal light immediately after each plasma pulse is enhanced compared to the background light. The integrated intensities after each pulse are subtracted and is proportional to the trace metal density. The detectors can be, for example, a CCD camera, a photo diode array, or a photomultiplier. The instrument is calibrated by measuring a known amount of trace metal vapor in a gas stream.

An absorbent can be utilized to collect the trace metal of interest and subsequently released for analysis. The absorbent will collect the trace metal and not much of the gas flow. This use of an absorbent is particularly effective in the collection of trace metal, mercury e.g., vapor in gas streams. The trace metal is collected with the absorbent at a pressure below atmosphere (40–300 Torr) to prevent the accumulation and condensation of water vapor near the absorbent. The collection time is less than 2 minutes and analysis time is less than 30 seconds. The trace metal is released by heating the absorbent. The gas flow (0.1–1 ml/min) is changed to either argon or nitrogen gas to deliver the trace metal to the plasma source, and produce a plasma in the source with a small emission background compared to the trace metal signal by reducing the levels of oxygen in the plasma source. In this configuration the absorbent eliminates problems with pressure fluctuations in the plasma source, reduces background emission and quenching problems, and ultimately increases signal-to-noise of the measurement. Furthermore, the absorbent can deal with the problem of large water vapor and acid content in the gas streams. For this configuration the plasma source is either pulsed or operated continuously. Although continuous plasma operation is not as detrimental with this second configuration, pulsed operation still has a significant advantage of reducing the competing emission background. The ultra-violet light emanating from the plasma is coupled to a spectrometer with either a fiber optic cable or a lens. The spectrometer resolves the light intensity from the trace metal line and the background light intensity near the trace metal line. These two light intensities are measured with detectors on the output of the spectrometer. The two intensities are subtracted and it is proportional to the trace metal density. The detectors can be a CCD camera, a photo diode array, or a photomultiplier. The instrument is calibrated by measuring a known amount of trace metal vapor in a gas stream.

A third configuration enables the measurement of metal content on particles in gas streams. The first two instrument configurations measure metals in the vapor phase in gas streams. The typical metals that have been measured were mercury, arsenic, and selenium because they are in the vapor phase for temperatures below 140 degrees C. The pulse operation of the plasma source doesn't provide sufficient average power to vaporize solid metals or break the bonds of molecular metals. The second configuration is modified (FIG. 4) to measure a larger number of metals that are typically in a solid form below 140 degrees C. (e.g. lead, chromium, magnesium, manganese, and zinc). A particle collection system is added to collect particles in gas streams and heat them to high temperatures (e.g., >1500 degrees F.) where they melt, their molecular bonds are broken, and they enter the vapor state. The particle collection system consists of a high temperature ceramic in the shape of a cylinder with a pin-hole in the bottom to allow the heated metals to stream out of the ceramic cylinder. The ceramic cylinder is porous to allow gas to be pulled through the ceramic pores, but trap the particles. The heating is achieved, for example, with 200 watts of AC power supply heating Nichrome wire wrapped around the ceramic cylinder. The particle collection system collects particles by pumping a gas stream loaded with particles through the ceramic cylinder. The gas stream flows into the ceramic cylinder, through the porous ceramic, and out a small pumping duct. The ceramic cylinder captures the particles and passes the gas stream. After collection, a non-porous ceramic shutter closes off the open end of the ceramic cylinder and a flow valve shuts off the gas stream collection. Next a purge gas bottle supplies purge gas to the ceramic cylinder through its porous walls. Then the AC power supply heats the Nichrome wire and, through conduction, heats the ceramic cylinder to temperatures in excess of 1500 degrees F. When the particles in the ceramic cylinder reach these temperatures the metals will melt, boil off, and exit the ceramic cylinder as a vapor and into the plasma source. The ultra-violet light emanating from the plasma is coupled to a spectrometer with a fiber optic cable, a lens, or both. The spectrometer resolves the light intensity from the metal lines and the background light intensity near the metal lines. These two light intensities are measured with detectors on the output of the spectrometer. The two intensities are subtracted and the difference is proportional to the metal density. The detectors can be a CCD camera, a photo diode array, or a photomultiplier. The instrument configuration can be used to analyze fly ash in coal fired utility plants, contaminated soil, or particulate from manufacturing plants.

These and other features of the invention will be more fully understood by reference to the following drawings.

DETAILED DESCRIPTION OF THE INVENTION

During the course of this description like numbers will be used to identify like elements accordingly to the different figures that illustrate the invention.

Figure 1A:
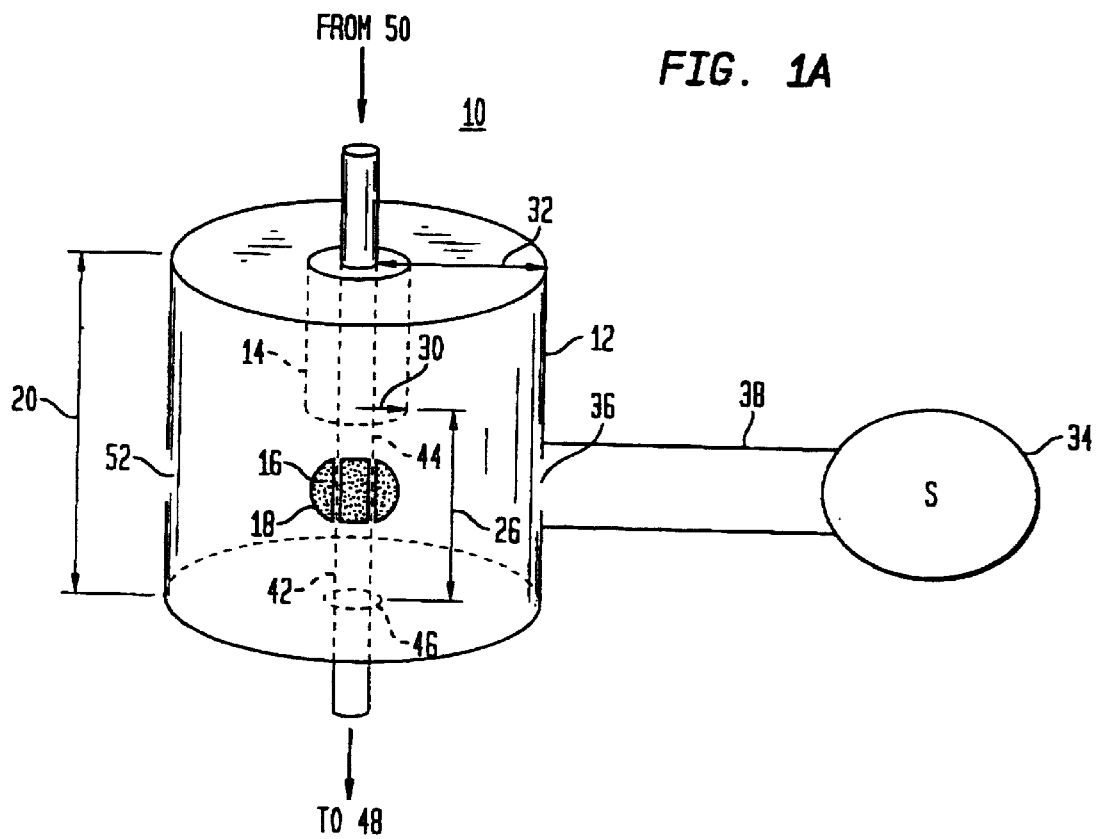
FIG. 1a. is a schematic of plasma source with a quartz tube.
Figure 1B:
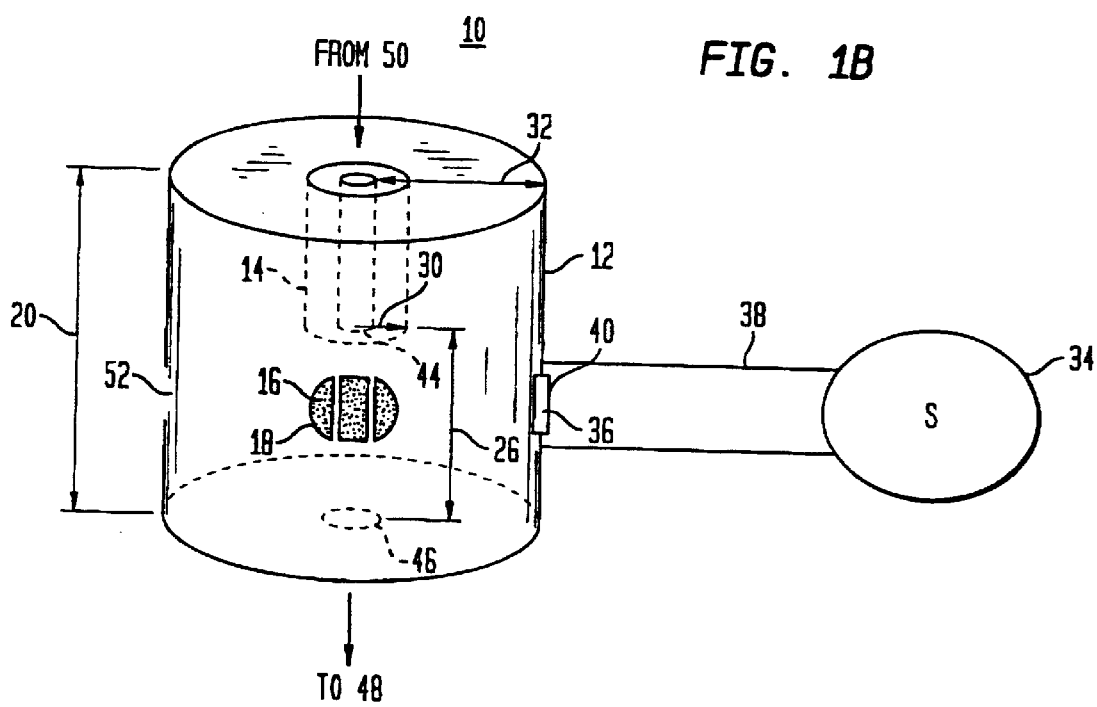
FIG. 1b. is a schematic of plasma source with a quartz window in the waveguide.

The plasma source 10 is based upon a resonant-high-intensity reentrant microwave cavity 12 (FIGS. 1a & 1b). The reentrant cavity 12 is a cylinder in shape with a coaxial center conductor 14 connected at one end of the cylinder and on the other end is a small gap 16. The plasma 18 is formed in the small gap 16 area and makes the reentrant microwave cavity 12 behave like a coaxial cavity. The height 20 of the cavity is adjusted to match the resonant condition for a pure coaxial cavity:

$$Z = \tfrac{1}{4}\lambda.$$

Z is the height of the cavity 20 and $\lambda$ is the wavelength of the input microwaves. The height of the gap 26 is adjusted to match the resonant condition for the reentrant cavity 12:

$$\frac{Ca\lambda}{2\varepsilon d} = \tan(b/a).$$

C is the speed of light, a is the radius 30 of the gap 16, b is the radius 32 of the reentrant.

Matching of these two conditions ensures that the plasma source will always be in resonance with the microwave generator 34 either with or without plasma 18 in the gap 16. There is a small aperture 36 in the cavity's wall for the microwave power to flow into the cavity 12 from the microwave generator 34. The microwave power flows through a waveguide 38 that is connected to the microwave cavity 12. There is a quartz window 40 in the waveguide to provide a vacuum seal and allow the transmission of the microwave power from the generator 34 to the plasma source 10 (FIG. 1b). Alternately, the window can be replaced in the cavity 12 by a circular quartz tube 42 mounted through a hole 44 in the center conductor and a hole 46 in the bottom of the cavity 12 (FIG. 1a). In addition, the waveguide 38 can be simply replaced with a coaxial cable feed from the generator 34. The plasma source 10 can be designed to operate in the range of 30–10,000 MHz. A pump 48 is used to pull a gas stream 50 into the cavity 12. The gas stream 50 enters the cavity 12 through the quartz tube 42 and enters the plasma 18 region. A second aperture 52 in the plasma source 10 provides a means of coupling light out of the plasma 18 region. The gas stream 50 then exits the cavity 12 through a small hole 46 in the bottom of the cavity 12. The plasma source 10 can operate over a pressure range of 1 milli Torr to atmospheric pressure (760 Torr), preferably <50 Torr and >10 milli Torr. The plasma source 10 can also be built with cylindrical and other microwave cavities.

Figure 2:
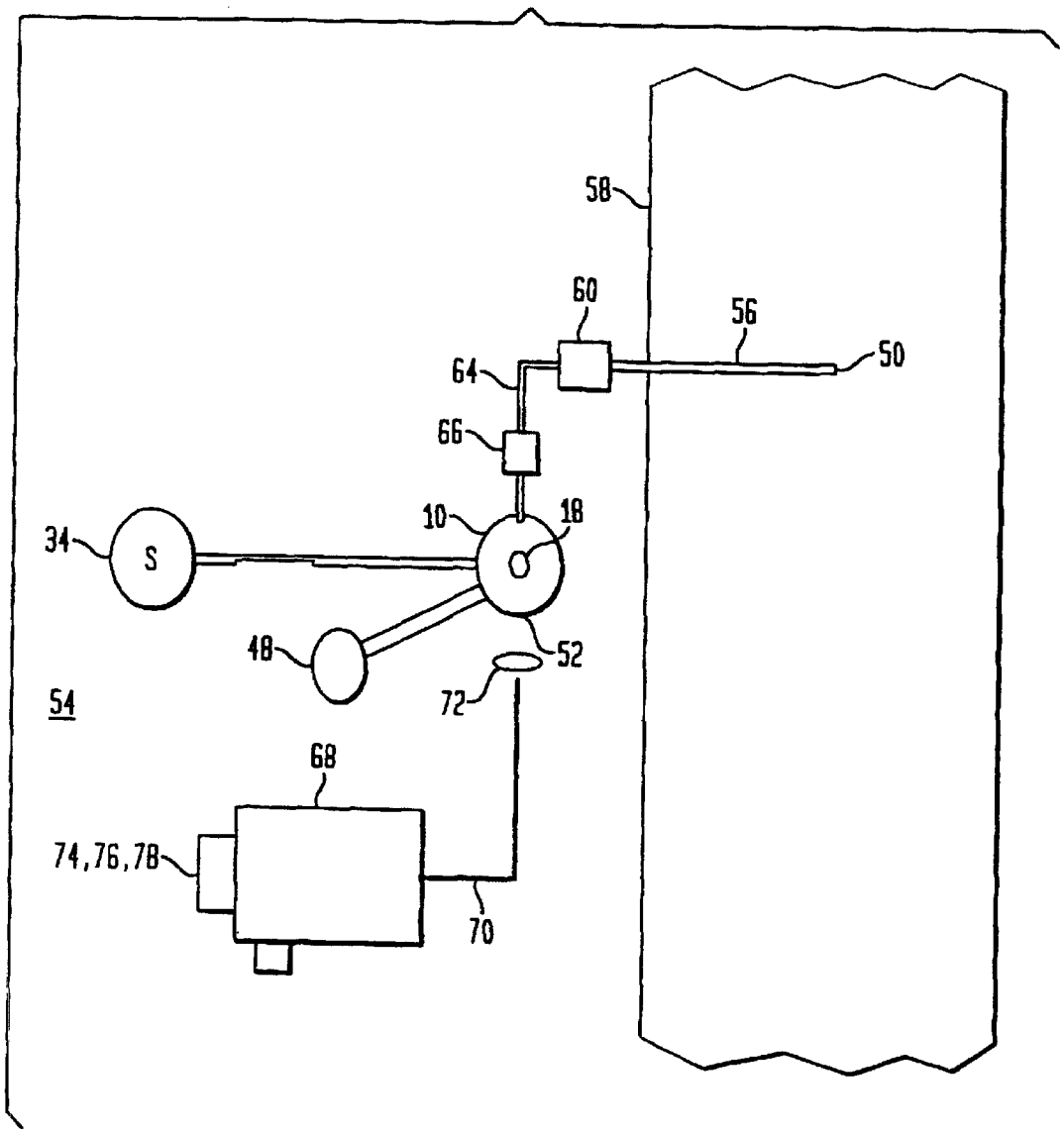
FIG. 2. is an illustration of a configuration for a device to measure metals in flue gas.

A first configuration 54 is shown in FIG. 2. A sampling probe 56 is mounted in a flue duct 58 to sample the gas stream 50. An optional filter 60 may follow the sample probe 56 to remove particulate matter from the gas stream 50. A sample line 64 delivers the gas stream 50 to the plasma 18 source. The sample line is preferably heated to a temperature greater than 212° F. preferably at least about 300° F. A flow meter or a flow restriction 66 before the plasma source 10 regulates the gas stream 50 flow. The gas stream 50 is pulled through the plasma source 10 with a pump 48. The plasma source 10 is driven with a microwave generator 34. The plasma source 10 is pulsed, for example by pulsing the power supply, to enhance the trace metal signal compared to plasma emission background. The ultra-violet light emanating from the plasma 18 is coupled to a spectrometer 68 with either a fiber optic cable 70, a lens 72, or both. The spectrometer 68 resolves the light intensity from the trace metal line (e.g., near 253.65 nm for mercury±2 nm) and the background light intensity near the trace metal line. These two light intensities are measured with detectors on the output of the spectrometer 68. The two light intensities are integrated over many pulses with averaging techniques e.g., box car averaging. The trace metal light immediately after each plasma pulse is enhanced compared to the background light. The integrated intensities after each pulse are subtracted and is proportional to the trace metal density. The detectors can be, for example, a CCD camera 74, a photo diode array 76, or a photomultiplier 78. The instrument is calibrated by measuring a known amount of trace metal vapor in a gas stream 50. The instrument 54 can sample gas streams 50 at a rate of about 1 to about 50 liters/min. The plasma source 10 produces the largest response to the trace metals when it operates at pressures in the range of 0.5 to 50 Torr.

A second configuration 80 (FIG. 3) utilizes an absorbent 82, such as, activated carbon, to collect the trace metal. A sampling probe 56 is mounted in a flue duct 58 to sample the gas stream 50. An optional filter 60 may follow the sample probe 56 to remove particulate matter 62 from the gas stream 50. A heated sample line 64 delivers the gas stream 50 to the absorbent 82. The absorbent 82 will collect the trace metal but very little of the other species in the gas stream 50. A high flow rate pump 84 pulls the gas stream 50 from the flue gas stack 58, and a flow-monitor 86 measures the flow rate during the gas sampling. The trace metal is collected with the absorbent 82 at a pressure below atmosphere (40–300 Torr) to prevent the accumulation and condensation of water vapor near the absorbent 82. A typical collection time is less than about 2 minutes and analysis time is less than about 30 seconds. After trace metal collection on the absorbent 82 is completed, two 3-way flow valves 88 are switched for the analysis of the trace metal collected by the absorbent 82. Release of the trace metal can be facilitated by heating the absorbent 82. The gas flow (0.1–1 ml/min) is changed to either argon or nitrogen gas which can be supplied from a purge-gas bottle 90 to deliver the trace metal to the plasma source 10, and produces a plasma 18 in the plasma source 10. The plasma 18 produced in this manner has a small emission background near the trace metal line in the plasma source 10. The gas flow from the purge gas bottle 90 is regulated with, e.g., an orifice 92 or a needle valve 94. A pump 48 pulls the purge gas through the plasma source 10 and maintains a pressure of 1–5 Torr in the plasma source 10. The plasma source 10 is driven with a microwave generator 34. In this configuration 80 the absorbent 82 eliminates problems with pressure fluctuations in the plasma source 10, removes background emission and quenching problems, and ultimately increases the signal-to-noise ratio of the measurement. Furthermore, the absorbent 82 can deal with the problem of large water vapor and acid content in the gas streams 50. For this configuration the plasma source 10 is either pulsed or operated continuously. Although continuous plasma operation is not as detrimental with this second configuration 80, pulsed operation still has a significant advantage in reducing the competing emission background. The ultra-violet light emanating from the plasma 18 is coupled to a spectrometer 68 for example, with either a fiber optic cable 70, a lens 72, or both. The spectrometer 68 resolves the light intensity from the trace metal line and the background light intensity near the trace metal line. These two light intensities are measured with detectors on the output of the spectrometer 68. The two intensities are subtracted and the difference is proportional to the trace metal density. Examples of the detectors include a CCD camera 74, a photo diode array 76, and a photomultiplier 78. The instrument is calibrated by measuring a known amount of trace metal vapor in a gas stream. The second configuration 80 of the instrument can sample gas streams 50 at a rate of 1 to 50 liters/min. The plasma source 10 produces the largest response to the trace metals when it operates at pressures in the range of 0.5 to 50 Torr and instrument flow rates during the desorption of the absorbent 82 in the range of 0.25 to 3000 milliliters/min.

Linearity & Sensitivity Measurements

Figure 5:
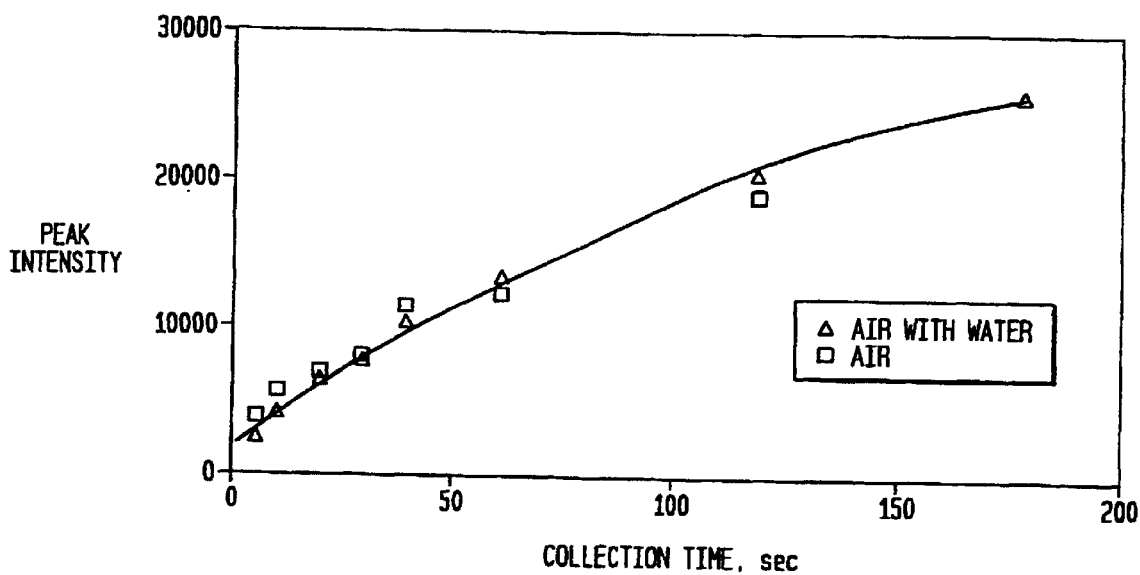
FIG. 5. is a data table showing the linearity and sensitivity of the device to measure metals in flue gas.

A continuous emissions monitor using the above second configuration 80 for the measurement of total mercury in flue gas was used to calculate linearity and sensitivity. Laboratory studies using bottled flue gas and mercury from a calibrated delivery system determined the measurement sensitivity and linearity for the second configuration 80 by collecting as containing different amounts of mercury The results are shown in the table in FIG. 5. The instrument linearity and sensitivity was observed over a range of mercury concentrations of 0.3–14 $\mu g/m^3$. For collection times longer than 60 seconds the response was no longer linear. For other configurations using absorbent 82 the linearity has been observed with concentrations above 100 $\mu g/m$. The instrument is sensitive to mercury concentrations as small as 0.1 $\mu g/m^3$ with a signal-to-noise of 3. FIG. 5 also shows that the response of the instrument is not affected by the presence of water vapor in the flue gas.

Figure 4:
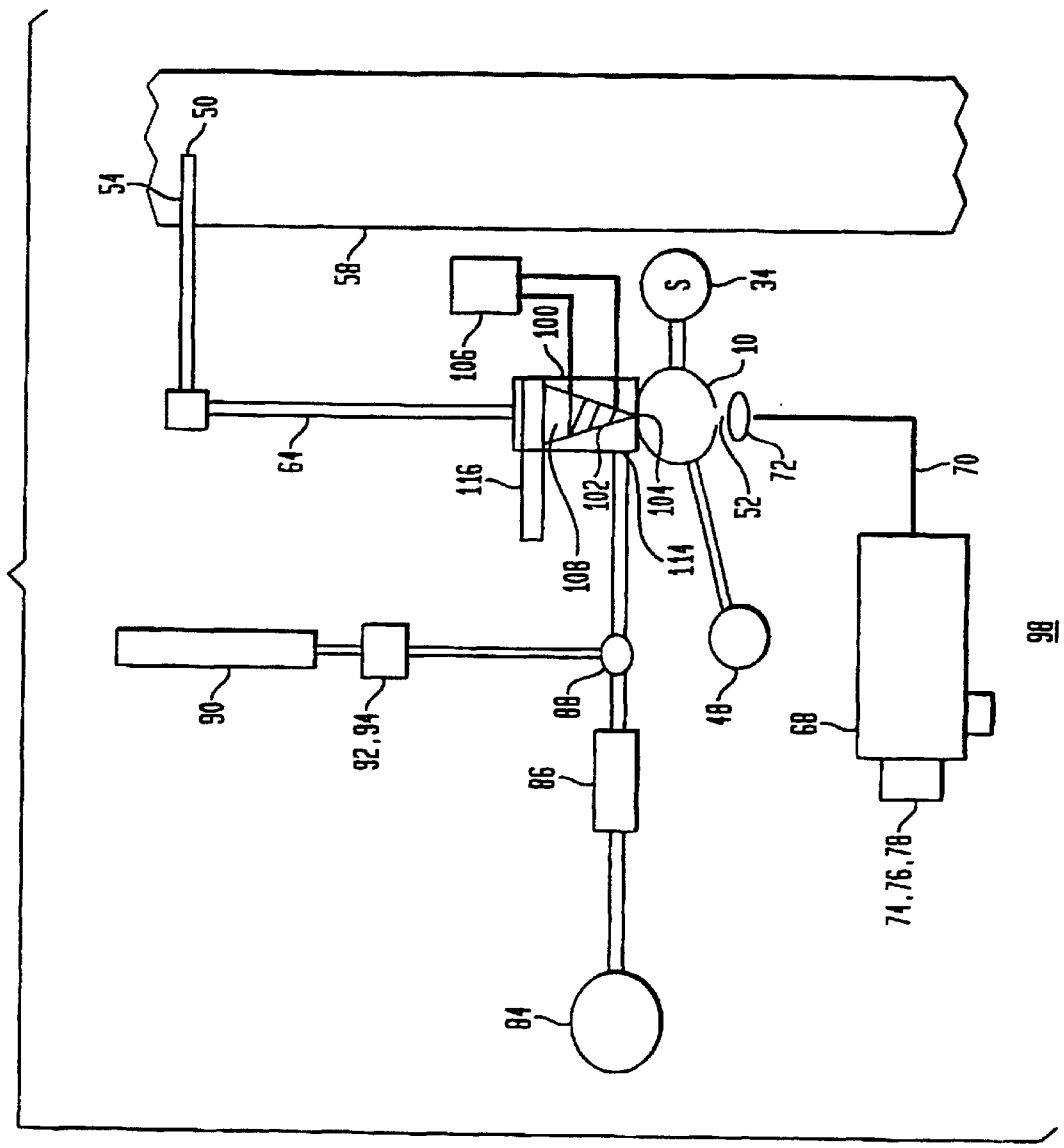
FIG. 4. is an illustration of a configuration for a device for measuring the metal content on particles.

Still yet another configuration 98 (FIG. 4) enables the measurement of metal content on particles 62 in gas streams. The first two instrument configurations 54, 80 measure metals in the vapor phase in gas streams. The typical metals that have been measured were mercury, arsenic, and selenium because they are in the vapor phase at temperatures below 140 degrees C. The pulse operation of the plasma source 10 doesn't provide sufficient average power to vaporize solid metals or break the bonds of molecular metals. The second configuration 80 is modified (FIG. 4) to measure a larger number of metals that are typically in a solid form below 140 degrees C. (e.g. lead, chromium, magnesium, manganese, and zinc). A particle collection system 100 is added to collect particles 62 in gas streams 50 and heat them to high temperatures (>1500 degrees F.) where they melt, their molecular bonds are broken, and they enter the vapor state. The particle collection system 100 consists of a high temperature ceramic container 102 with a pin-hole 104 in the bottom to allow the heated metals to stream out of the ceramic container 102. The ceramic container 102 is porous to allow gas to be pulled through the ceramic pores, but still trap the particles. The particle collection system 100 is mounted very close to the plasma source 10 to enable the efficient delivery of the hot metal vapor to the plasma source 10. The heating was achieved with a 200 watts of AC power supply 106 heating Nichrome wire 10 wrapped around the ceramic container 102. Alternately the metals can be heated in a gas furnace, or with wave power. The particle collection system 100 collects particles 62 by pumping a gas stream 50 loaded with particles 62 through the ceramic container 102. The gas stream 50 flows into the ceramic container 102, through the porous ceramic, and out a small pumping duct 114. The small pumping duct 114 is connected to a high flow rate pump 84 to pull the gas stream 50 through the ceramic container 102. The ceramic container 102 captures the particles and passes the gas stream 50. After collection, a non-porous ceramic shutter 116 closes off the open end of the ceramic container 102 and a thee-way flow valve 88 terminates the gas stream 50 collection and a purge gas is delivered to the ceramic container 102. A purge-gas bottle 90 supplies purge gas to the ceramic container 102 through its porous walls. The gas flow from the purge gas bottle is regulated with an orifice 92 or a needle valve 94. A pump 48 pulls the purge gas through the plasma source 10 and maintains a pressure of 1–5 Torr in the plasma source 10. The AC power supply 106 heats the Nichrome wire 108 and through conduction heats the ceramic cylinder 102 to temperatures in excess of 1500 degrees F. When the particles in the ceramic container 102 reach these temperatures the metals will melt, boil off, and exit the ceramic container 102 as a vapor and into the plasma source 10. The plasma source 10 is connected to a pump 48 to pull the purge gas into the plasma source 10. The plasma source 10 is driven with a microwave generator 34. When the metals enter the plasma 18 it produces light proportional to each metal's density. The ultra-violet light emanating from the plasma 18 is coupled to a spectrometer 68 with either a fiber optic cable 70, a lens 72, or both. The spectrometer 68 resolves the light intensity from the metal lines and the background light intensity near the metal lines. These two light intensities are measured with detectors on the output of the spectrometer 68. The two intensities are subtracted and the difference is proportional to the mercury density. The detectors can be a CCD camera 74, a photo diode array 76, or a photomultiplier 78. The particles 62 can be collected at gas flow rates of 1 to 50 l/min. The plasma source 10 produces the largest response to the trace metals when the metals are delivered with the purge gas flow rate in the range of 0.25 to 50 milliliters/min. The instrument configuration can be used to analyze fly ash in coal fired utility plants, contaminated soil, or particulate 62 from manufacturing plants.

Measurement of Metals on Fly Ash

Figure 6:
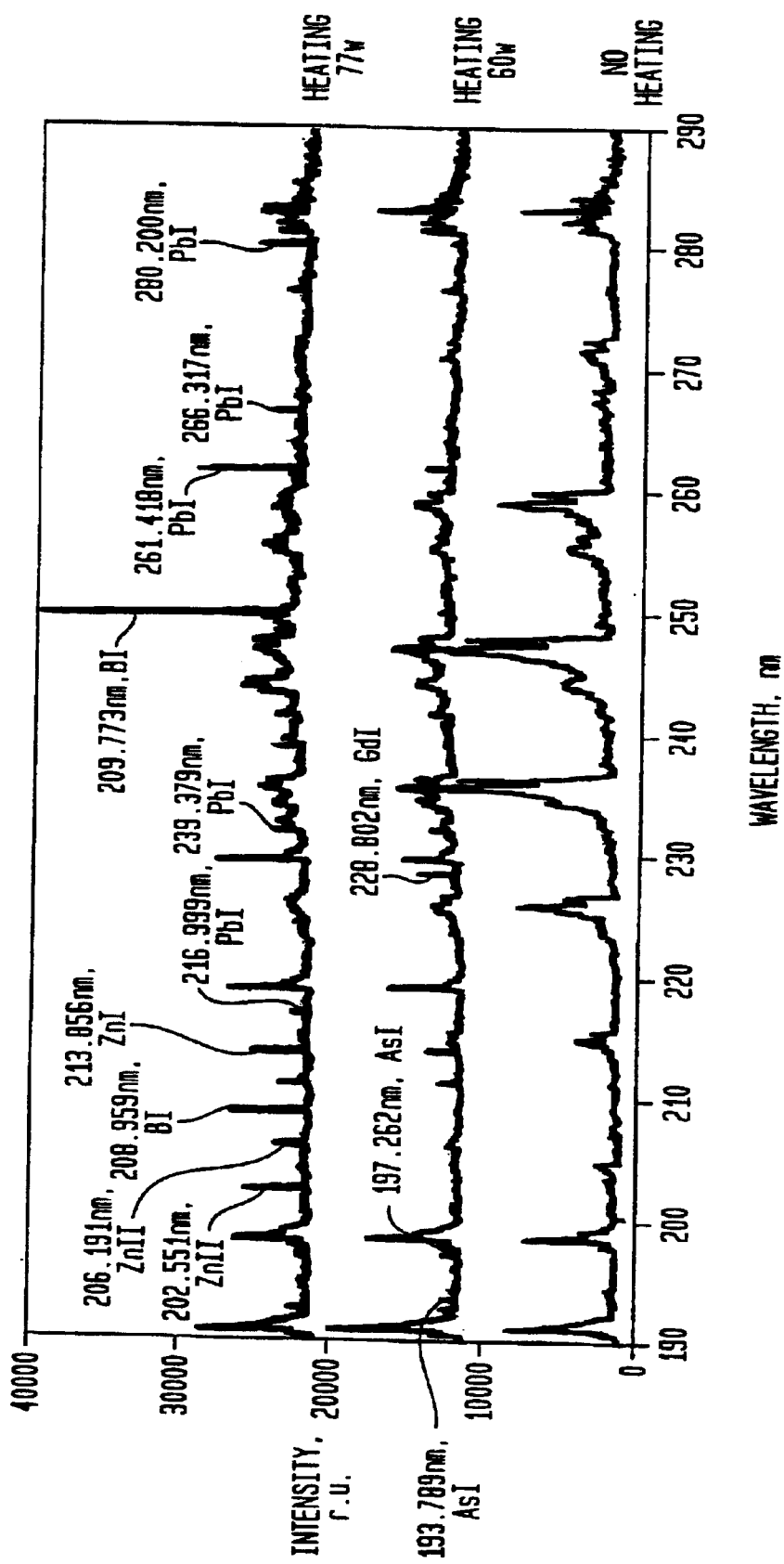
FIG. 6. shows measurements of metal spectra from fly ash.

The configuration 98 was tested in the laboratory for its ability to identify the metals on fly ash. Fly ash is the particle dust coming out of coal-fired utility plants. One-tenth $cm^{-3}$ volume of fly ash was loaded into the particle collection system 100. The AC power supply 106 was turned on and a ceramic cylinder 102 was heated to temperatures in excess of 1500 degrees F. A purge gas bottle 90 supplied the purge gas to the ceramic cylinder 102 through its porous walls. When the metals entered the plasma 18 light proportional to each metal's density was produced. The ultra-violet light emanating from the plasma 18 was coupled to a spectrometer 68 with a fiber optic cable 70. A CCD camera 74 was used to measure the emission spectrum resolved by the spectrometer 68. FIG. 6 shows measured spectra. The spectrum shows the measurement of arsenic, lead, zinc, boron, and cadmium. The third configuration 98 was also used to measure chromium, iron, magnesium, mercury, and manganese. The third configuration 98 is not limited to these metals and can be used to analyze fly ash in coal fired utility plants, contaminated soil, or particulate from manufacturing processes.

Reduction of Background Emission

Figure 7:
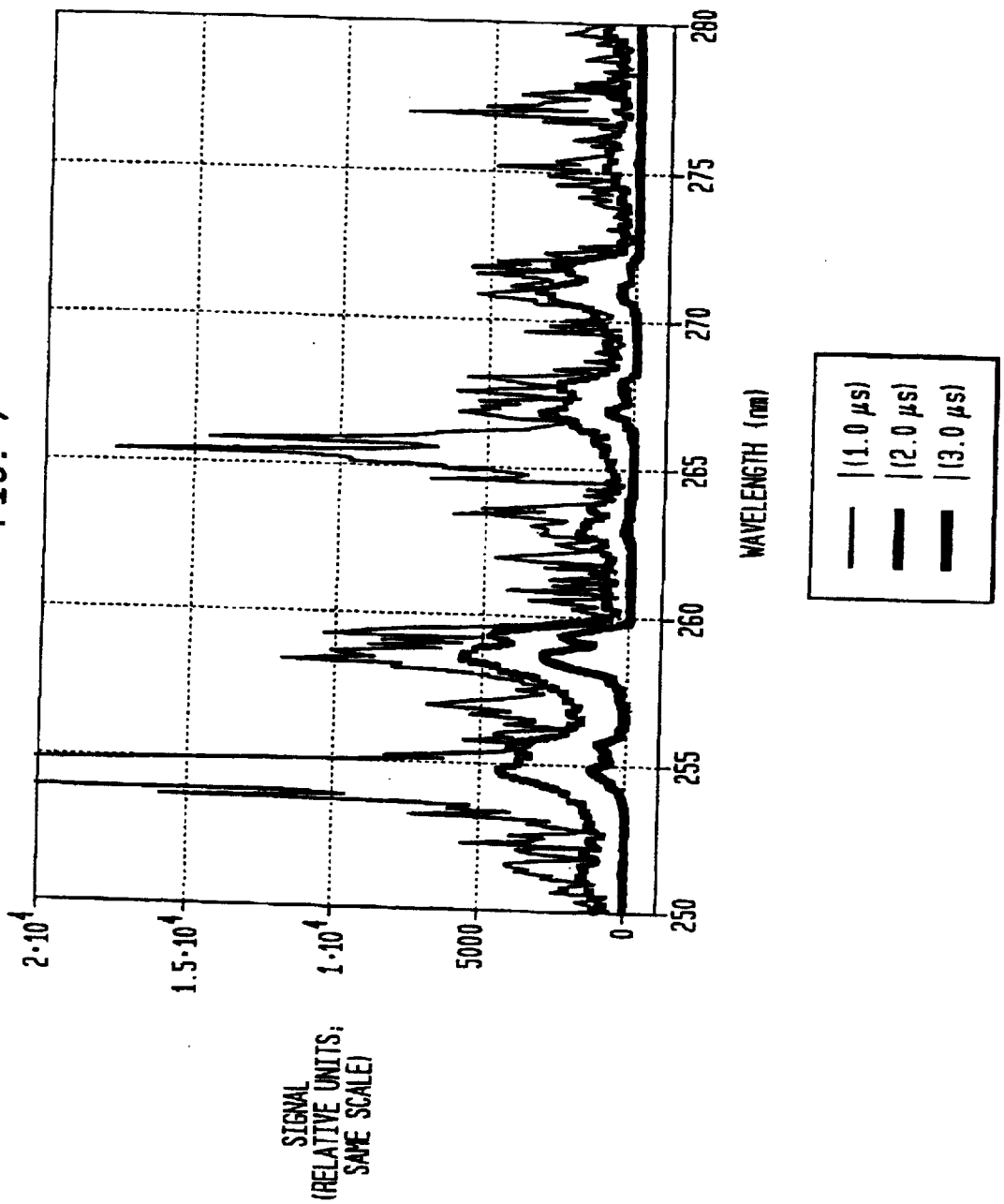
FIG. 7. is the emission spectra near the 253 nm mercury line from nitrogen-oxygen plasmas of different pulse duration.

One aspect of this invention utilizes pulsed plasma for reducing the background emission spectrum of plasmas 18. The reduction can be enhanced by pulsing the plasma and simultaneously operating at low pressure. The pulses are 0.2–10 microseconds in duration with a repetition rate near 1 kHz. The operating pressures are less than 100 Torr. The method will work with pulse durations less than 100 microseconds and repetition rates less than 100 kHz. When not using the method of this invention, plasma sources operate at high operating temperatures and high pressures that tend to greatly enhance chemical reactions. This is particularly true when the gas stream includes a strong oxidizer, like oxygen, fluorine, and chlorine. In many cases the products of the chemical reactions are responsible for background emission observed in plasma sources. For example, plasma sources continuously operating with oxygen-nitrogen gas streams results in the creation of oxides of nitrogen. Oxides of nitrogen create a large emission background near the mercury 253.65 nm line and tends to mask the mercury emission. A nitrogen gas stream with only 0.5% oxygen in a plasma is sufficient to create a large background near the mercury line at 253.65 nm. FIG. 7 shows a series of spectra near the mercury line (253 nm) measured by the first configuration 54 with the microwave plasma source 10 operating in a pulsed mode. For these spectra, the microwave pulses are 10 microseconds wide at a rate of 1 kHz, and the operating pressure is 10 Torr. The first spectrum is 1 microsecond after the beginning of the microwave pulse. The emission background levels are very low. The next two spectra which are one and two microseconds later in time, produce significantly more emission background, and are due to the production of oxides of nitrogen. Later in time the spectra are larger. The emission spectrum is extremely large when the plasma source 10 operates continuously. Therefore, by limiting the pulse length, the emission background spectrum near the mercury line can be reduced to very low levels. Operating at low pressure also helps reduce these emissions because the gas doesn't collide as often with the plasma 18, preventing the gas from heating. Small pulses on the order of 1–5 microseconds at a rate of 2–4 kHz introduces only 3–30 watts of average power to the plasma 18. Therefore, there is very little energy to heat up the gas and produce oxides of nitrogen.

With the plasma source 10 operating in a pulsed mode, all of the light can be collected for a measurement of mercury or any other metal. However, when measuring mercury the mercury signal extends after the end of the plasma pulse, but the background light is extremely small. The plasma 18 slowly decays after the pulse and is sometime referred to as the "after glow". During this time the mercury signal at its, characteristic wavelength of 253.65 nm has its best signal-to-background due to the emission from the oxides of nitrogen. The detected signal after every pulse is box-car-averaged for some 100,000 pulses to measure mercury in concentrations on the order of 100 parts per trillion. This technique is applicable to all plasma sources.

Reduction of Quenching

Another aspect of the invention reduces metal emission quenching. Quenching is a process where a molecular specie in the plasma 18 takes the energy of the electrons that normally excite the specie of interest by means of collisions. Quenching dramatically limits trace metal line emission in gas streams 50 containing oxygen, nitrous oxide, carbon monoxide, and carbon dioxide. In a particular example, mercury emission near 253 nm is suppressed due to oxygen, carbon monoxide, nitrous oxide, and carbon dioxide. The effect is dramatic and only 1% oxygen at atmospheric pressure is sufficient to suppress the mercury emission. However, by operating at low pressures, below 100 Torr, the concentrations of the quenching gases are lower and the collisions with the quenching gases are less frequent. Consequently, the quenching process is reduced. At pressures below 30 Torr, quenching is not much of a factor and the trace metal emission is greatly enhanced. A preferred pressure for operation of the first 54 and second 98 configurations is near about 1 Torr. In general, quenching of emission is a well-known physical effect, however; the quenching of the mercury emission at the 253.65 nm wavelength due to the quenching of oxygen, nitrous oxide, carbon monoxide, or carbon dioxide is something discovered in the development of the present invention. This low-pressure operation unexpectedly improves the instrument sensitivity by a factor of 10,000. Alternately, the plasma source can be operated with non-quenching gases. Pure nitrogen and argon are not a quenching molecules for mercury at the 253.65 nm wavelength. The second configuration uses the absorbent 82 that collects mercury in gas streams 50 containing quenching gases, but operates the plasma source 10 with the non-quenching gases of argon or nitrogen. Non-quenching gases are supplied to the plasma source 10 by the purge-gas bottle 90 in the second configuration 98.

Metal Emission Enhancement

Figure 8A:
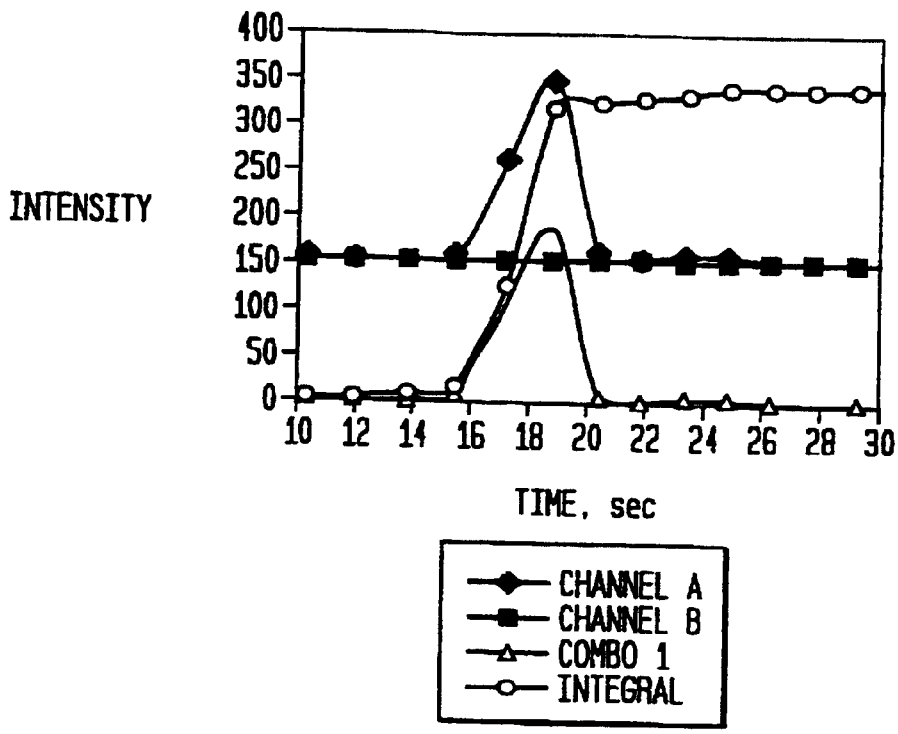
FIG. 8. illustrates a comparison of small and large gas flow rates in the operation of the plasma source to generate light from mercury.
Figure 8B:
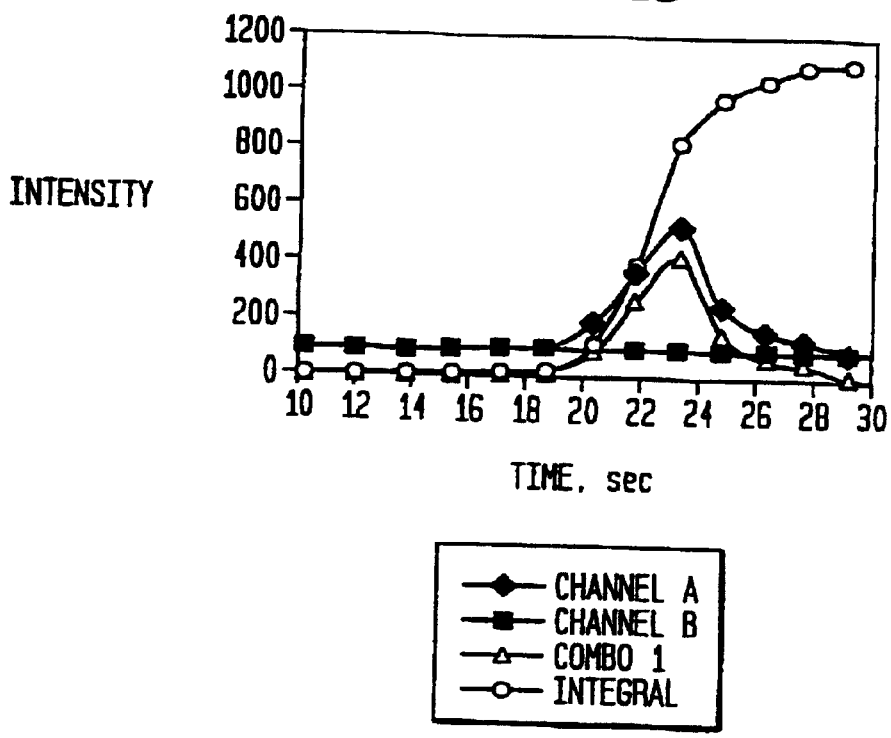

Another aspect of the invention enhances the metal emission by operating the plasma source 10 with an extremely small gas flow (0.1–1 ml/min). This can be achieved in practice in the second configuration 9 (FIG. 3), by using an absorbent 82. Using the absorbent 82 enables sampling of flue gas at high flow rates (2–30 liters/min) and pressures (40–760 Torr), and then analysis at low gas flow rates (0.1–1.0 ml/min). In addition, the analysis can be conducted the low pressures (1–40 Torr), where it is optimum with the plasma source 10 The metals released from the absorbent 82 are entrained in the gas flow going to the plasma source 10. A small gas flow results in the metals taking a longer period of time to flow through the plasma 18; the more time a metal atom is in plasma 18, the more emission the metal atom will emit. The amount of emission determines the measurement sensitivity. Consequently, the small gas flow during analysis greatly improves the instrument sensitivity. FIG. 8 compares the light intensity of an example 253 nm mercury line emission generated by a fixed amount of mercury passing through the plasma source at gas flow rates of 5 and 0.5 ml/min. FIG. 8 is plotted as a function of time after the start of absorbent 82 heating to release the metals. The smaller gas flow results in a larger light intensity that continues for a longer period of time.

There are additional benefits in operating the plasma source 10 as described above. The combination of low pressure and pulsed operation of the plasma source 10 also has the benefit of lowering the average microwave power required to operate the plasma source 10 to a mere 15 watts. This dramatically reduces the cost of the microwave generator 20. The use of an absorbent 82 has the added benefit of isolating the plasma source 10 from pressure fluctuations and quenching gases that are in gas streams 50 found in flue gas. In addition, it helps concentrate the metal to improve the signal to noise of the metal measurement.

Operational Experiments at a Coal-Fired Utility Plant

Figure 3:
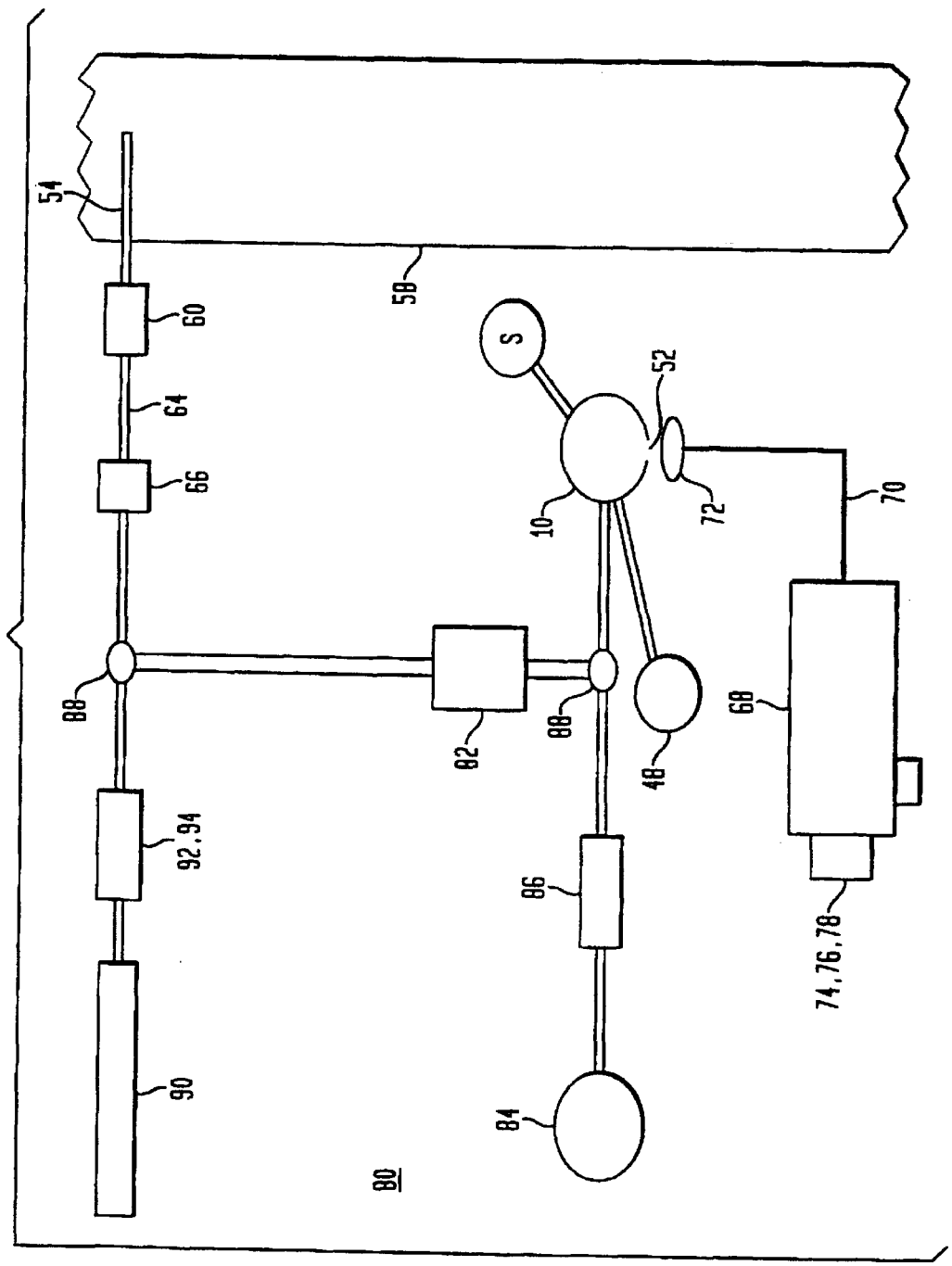
FIG. 3. is an illustration of a configuration for a device to measure metals in flue gas with an absorber.

Field measurements were completed at a (300 MW) wet-bottom electrical generating boiler burning eastern bituminous low-sulfur coal. The second configuration 80 was used during these field tests (FIG. 3). A probe 56 was placed in the duct 58 at the output of the precipitator. Although a filter 60 was shown in the figure to remove particles from the gas stream 50, none was used during these field tests. Past the precipitator there was little fly ash. The instrument 80 was mounted adjacent to the duct 58 to keep the heated sample line 64 as short as possible (<4 feet). The. gas flow into the plasma source 10 is controlled with a standard vacuum pump 32. The UV measurements were made through a quartz window on the plasma source 10. A fiber optic cable 70 transports the light into the spectrometer 68 with an ultra-violet CCD detector 74. The field tests were made over one month time period. Two spectrometers 68 were used simultaneously during these experiments: an Acton 300i spectrometer and an Ocean Optics 2000 Series spectrometer. The microwave source 34 produced 1-microsecond pulses at a rate of 4000 per second. The microwave source 34 frequency is 2.45 GHz. The plasma source 10 was operated at a pressure of 2 Torr and at flow rates in the range of 0.2–1.0 ml/min.

Experiment 1

The power plant was producing 314 MW of electrical power at the time of the measurements. The plant burned a combination of 92% coal and 8% natural gas. The heated sample line was held at a temperature near 100 degrees C. The measured mercury concentration was only 0.3 $\mu g/m^3$. The measurements were low because the sample line was not heated to the flue gas temperature in the duct of 140 degrees Centigrade.

Experiment 2

The plant produced 29 MW of electrical power at the time of the measurements. The plant burned 90% coal and 10% natural gas. The measurements were completed with the sample line at the flue gas temperature of 140 degrees C. The mercury concentration was measured to be values of 0.9 and 1.0 $\mu g/m^3$. The measurements became reproducible with the sample lines heated at 140 degrees Centigrade.

Experiment 3

The power plant was producing 270 MW of electrical power on at the time of the measurements. The plant burned 100% coal. The heated sample line was held at a temperature near 140 degrees C. The measured mercury concentrations were 0.7 and 0.6 $\mu g/m^3$.

Experiment 4

The power plant was producing 300 MW of electrical power on at the time of the measurements. The plant burned 100% coal. The heated sample line was held at a temperature near 140 degrees C. The measured mercury concentrations were 0.9, 1.4, and 1.25 $\mu g/m^3$.

Experiment 5

The power plant was producing 275 MW of electrical power on at the time of the measurements. The plant burned 100% coal. The heated sample line was held at a temperature near 140 degrees C. The measured mercury concentrations were 1.2 and 1.3 $\mu g/m^3$.

The conclusion of Experiments 1–5 was that it is essential to maintain the heated sample lines 64 at temperatures at or greater than the gas streams 50 being sampled from the flue duct 58. At these temperatures, the mercury concentrations were reproducible and in the range of 0.6–1.4 $\mu g/m^3$. Previous measurements of the mercury concentration at this facility using wet chemistry techniques were near 1.5 $\mu g/m^3$. The mercury levels measured by the instrument were calibrated with a NIST standard mercury source whose concentration was verified by independent laboratory analysis. The field measurements were more than a factor of 10 above the instrument's 80 minimum detection level. The first configuration 54 was used during the field tests to detect arsenic and selenium in the flue gas.

Experiment 6

Figure 9:
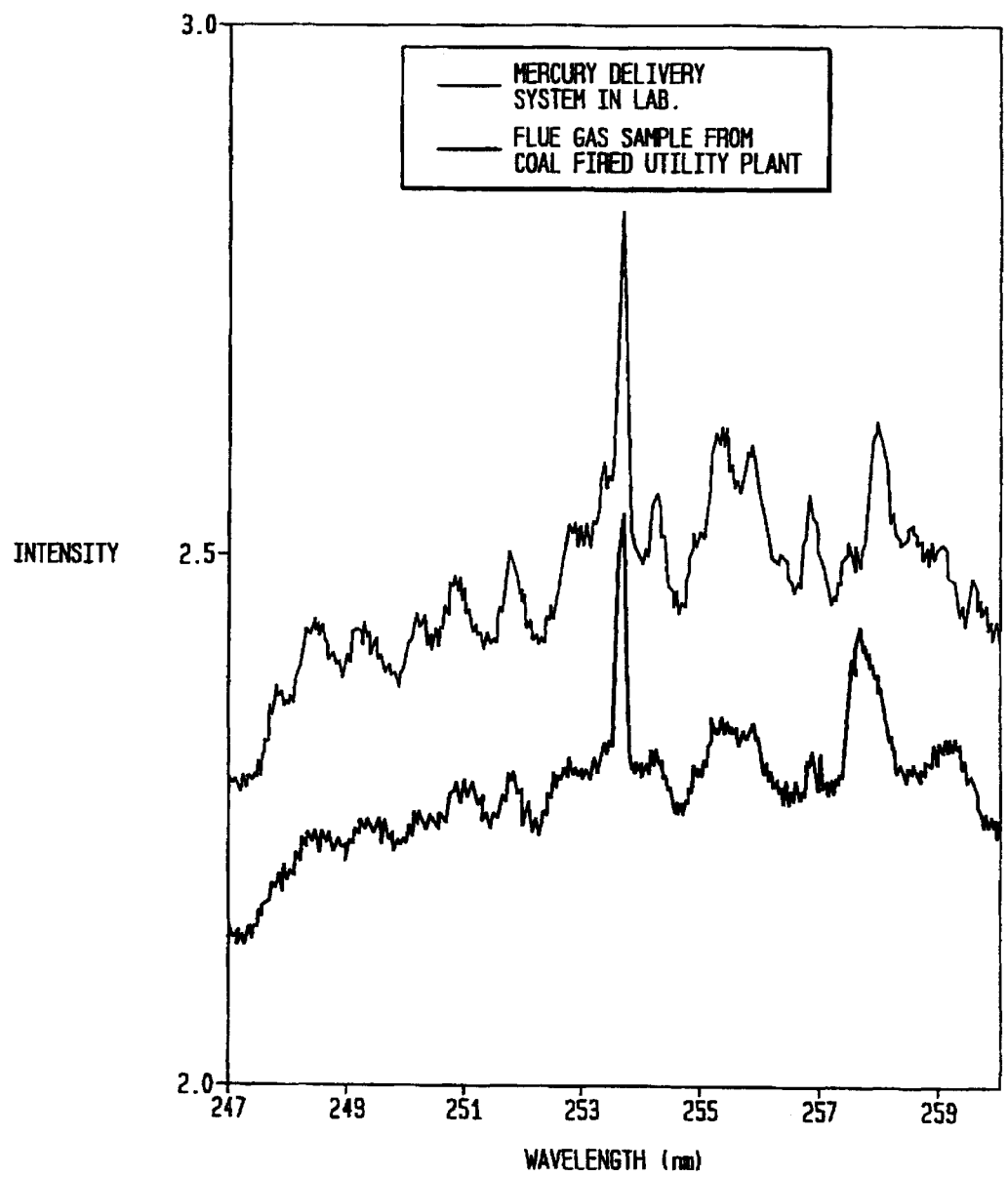
FIG. 9. shows the measured spectra near the 253.65 nm mercury line from the two different sources of mercury: laboratory calibration source and coal-fired electric utility plant.

To verify that the signals produced by the second configuration 80 in the field tests at a coal-fired utility plant were only due to mercury and were not compromised by UV emission from another element near the same wavelength, a UV CCD camera 74 was mounted on the spectrometer 6. Measurements with the CCD camera 74 were made in the field and in the laboratory. FIG. 9 shows the measured spectra near the 253.65 nm mercury line from measurements completed in the field and the laboratory. The spectra 140 are nearly identical and clearly show a large mercury line at the appropriate wavelength, verifying the laboratory and field measurements are indeed due to only mercury and there is no complication of emission from another element. Two spectrometers 68 were used simultaneously during these experiments: an Acton 300i spectrometer and an Ocean Optics 2000 Series spectrometer. The microwave source 34 produced 1-microsecond pulses at a rate of 4000 per second. The microwave source 34 frequency is 2.45 GHz. The plasma source 10 was operated at a pressure of 2 Torr and at flow rates in the range of 0.2–1.0 ml/min.

While the invention has been described with reference to the preferred embodiment thereof, it will be appreciated by those of ordinary skill in the art that modifications can be made to the structure and method of the present invention without departing from the spirit and scope thereof.

What is claimed is:

1. A method for the detection of metals in a gas stream comprising the steps of:
    a) obtaining a sample of said gas stream;
    b) passing said sample of said gas stream through a plasma chamber at a predetermined rate of flow and pressure;
    c) exposing said sample of said gas stream within said plasma chamber to a plasma discharge resulting in the emission of a plasma light;
    d) transmitting said plasma light to one or more spectrometers;
    e) resolving the spectra of said plasma light with said one or more spectrometers;
    f) detecting the resolved light at said one or more spectrometers with one or more detectors;
    g) analyzing the detected light to determine a measurement of the metal content of said gas stream;
    h) repeating steps a) through g) one or more times;
    i) averaging the measurements obtained in each repetition of step f);
    wherein the signal-to-noise ratio of said metal content measurement, indicated by the comparison of the detected light emissions of said plasma light corresponding to the metal content of said gas stream sample and the detected light emissions of said plasma light corresponding to the non-metal content of said gas stream sample, is increased by enhancing the strength of the light emissions of said plasma light corresponding to the metal content of said gas stream sample, increasing the time that said sample of said gas stream is exposed to said plasma, decreasing the detected light emissions of said plasma light corresponding to the non-metal content of said gas stream sample, or any combination thereof.

2. The method of claim 1 wherein the detected light emissions of said plasma light corresponding to the non-metal content of said gas stream is decreased by pulsing said plasma.

3. The method of claim 2 wherein said plasma is pulsed at a frequency of about 2 to about 4 kHz.

4. The method of claim 2 wherein said plasma pulse duration is about 1 to about 5 microseconds.

5. The method of claim 2 wherein said plasma is a microwave plasma discharge.

6. The method of claim 1 wherein the strength of the light emissions of said plasma light corresponding to the metal content of said gas stream sample is enhanced by maintaining the pressure of said gas stream sample between about 1 milli Torr and about 760 Torr.

7. The method of claim 6 wherein said gas stream sample is at a pressure between about 10 milli Torr and about 50 Torr.

8. The method of claim 6 wherein said gas stream sample is at a pressure between about 1 and about 5 Torr.

9. The method of claim 1 wherein the time that said sample of said gas stream is exposed to said plasma is increased by maintaining the flow rate of said sample of said gas stream between about 0.1 to about 50 ml/min.

10. The method of claim 9 wherein said flow rate of said sample of said gas stream is between about 0.1 to about 1.0 ml/min.

11. The method of claim 9 wherein said flow rate of said sample of said gas stream is between about 0.2 to about 1.0 ml/min.

12. The method of claim 1 wherein said gas stream sample is obtained by diverting a partial gas stream from said gas stream to said plasma chamber.

13. The method of claim 1 wherein said sample stream is obtained by:
passing a partial stream diverted from said gas stream through an absorbent which removably absorbs said metals from said partial stream;
stopping the flow of said partial gas stream to said absorbent;
heating said absorbent to facilitate the desorption of said metals from said absorbent;
directing a flow of an inert gas through said absorbent and thereby removing the metal from said absorbent and incorporating it into said inert gas flow; and,
directing said metal containing flow to said plasma chamber;
wherein the absorbent is heated directly or by heating said flow of inert gas.

14. The method of claim 1 wherein said sample stream is obtained by:
passing a partial stream diverted from said gas stream through a porous particle collector which removes and collects any particles within said partial stream;
stopping the flow of said partial gas stream to said porous particle collector;
heating said particle collector to a temperature sufficient to vaporize any metal particles collected by said particle collector;
directing a low pressure flow of an inert gas through said particle collector, thereby incorporating any metal vapor into said inert gas flow; and,
directing said metal containing low pressure flow to said plasma chamber.

15. An apparatus for the detection of metals in a gas stream comprising:
a plasma chamber having an internal cavity, a gas flow input, a gas flow output, an energy input and a light output;
an energy source connected to said energy input;
one or more spectrometers having an input coupled to said chamber light output and an output;
two or more light intensity detectors coupled to said spectrometer output for measuring metal and non-metal content;
a pulsing means for said energy source;
a gas flow attenuation means for regulating the gas stream entering said gas flow input;
a pump means for maintaining the flow rate and pressure of said gas flow from said gas flow input, through said cavity and out of said gas flow output;
a means for sampling the gas stream and supplying the sample to said gas flow attenuation means;
wherein the signal-to-noise ratio indicated by the comparison of the measurement from the light intensity detectors corresponding to the metal content of said gas stream sample and the measurement from the light intensity detectors corresponding to the non-metal content of said gas stream sample, is increased by pulsing said energy source with said pulsing means, adjusting said gas flow attenuation means and said pump means to maintain a flow rate below about 50 ml/min, adjusting said gas flow attenuation means and said pump means to maintain a pressure below about 760 Torr.

16. The system of claim 15 wherein said cavity is a resonant-high-intensity reentrant microwave cavity and said energy source is a microwave generator.

17. The system of claim 15 wherein s a id energy source is a radio frequency wave generator.

18. The system of claim 16 wherein said microwave generator is coupled to said energy input with a waveguide.

19. The system of claim 15 wherein said sampling means comprises an absorbent means, an inert gas source capable of supplying an inert gas at varying rates and pressures, and one or more flow control means;
wherein a portion of the gas stream is diverted to and directed through said absorbent means thereby absorbing metal contained in said diverted gas stream;
wherein said one or more flow control means can be selectively configured individually or in a group, between a configuration which directs the diverted gas stream to said absorbent and a configuration which allows said inert gas through said absorbent and to said plasma chamber gas flow input.

20. The system of claim 15 wherein said sampling means comprises a particle collection means, a heating means, an inert gas source capable of supplying an inert gas at varying rates and pressures, and one or more flow control means;
wherein a portion of the gas stream is diverted to and directed through said particle collection means thereby removing and collecting particles of metal contained in said diverted gas stream;
wherein said heating means heats said collected metal particles to temperatures greater than 1500 degrees F. converting said particles into metal vapor;

wherein said one or more flow control means can be selectively configured, individually or in a group, between a configuration which directs the diverted gas stream to said absorbent and a configuration which allows said inert gas through said absorbent and to said plasma chamber gas flow input.

* * * * *